United States Patent
Costanzo et al.

(10) Patent No.: US 9,446,070 B2
(45) Date of Patent: Sep. 20, 2016

(54) NANOCERIA WITH CITRIC ACID ADDITIVE

(71) Applicant: Cerion Enterprises, LLC, Rochester, NY (US)

(72) Inventors: Wendi Ann Costanzo, Webster, NY (US); Kenneth Joseph Reed, Brighton, NY (US)

(73) Assignee: CERION, LLC, Rochester, NY (US)

( * ) Notice: Subject to any disclaimer, the term of this patent is extended or adjusted under 35 U.S.C. 154(b) by 23 days.

(21) Appl. No.: 13/838,332

(22) Filed: Mar. 15, 2013

(65) Prior Publication Data

US 2013/0337084 A1    Dec. 19, 2013

Related U.S. Application Data

(60) Provisional application No. 61/689,806, filed on Jun. 13, 2012.

(51) Int. Cl.
*A61K 9/51* (2006.01)
*A61K 33/24* (2006.01)

(52) U.S. Cl.
CPC .............. *A61K 33/24* (2013.01); *A61K 9/5123* (2013.01); *Y10S 977/773* (2013.01)

(58) Field of Classification Search
None
See application file for complete search history.

(56) References Cited

U.S. PATENT DOCUMENTS

| | | | |
|---|---|---|---|
| 4,599,201 A * | 7/1986 | Gradeff | C07C 51/412 423/21.1 |
| 7,534,453 B1 | 5/2009 | Rzigalinski et al. | |
| 8,883,865 B2 * | 11/2014 | DiFrancesco | B01J 13/0034 423/263 |
| 9,034,392 B2 * | 5/2015 | Reed | A61K 33/24 424/617 |
| 9,221,032 B2 * | 12/2015 | Reed | B01F 3/0807 |
| 9,303,223 B2 * | 4/2016 | Difrancesco | B01J 13/0034 |
| 2003/0032679 A1 * | 2/2003 | Cayton et al. | 516/33 |
| 2005/0142567 A1 * | 6/2005 | Su | G01N 21/6428 435/6.11 |
| 2008/0045401 A1 * | 2/2008 | Zhou et al. | 502/60 |
| 2010/0152077 A1 | 6/2010 | Allston et al. | |

FOREIGN PATENT DOCUMENTS

| | | |
|---|---|---|
| WO | WO 2007/002662 A2 | 1/2007 |
| WO | WO 2008/002323 A2 | 1/2008 |
| WO | WO 2008/030805 A1 | 3/2008 |
| WO | WO 2008/030815 A2 | 3/2008 |

OTHER PUBLICATIONS

YY Tsai, JO Cossio, K Agering, NE Simpson, MA Atkinson, CH Wasserfall, I Constantinidis, W Sigmund. "Novel Synthesis of Cerium Oxide Nanoparticles for Free Radical Scavenging." Nanomedicine, vol. 2(3), 2007, pp. 325-332.*

(Continued)

*Primary Examiner* — Isaac Shomer
(74) *Attorney, Agent, or Firm* — Ratnerprestia

(57) ABSTRACT

A process for making nanoparticles of biocompatible materials is described, wherein an aqueous reaction mixture comprising cerous ion, citric acid, an oxidant, and water, is adjusted to a predetermined range of pH, held at temperature conditions to directly form, without isolation, a stable dispersion of cerium oxide nanoparticles. Dispersions of these biocompatible cerium oxide nanoparticles exhibit self-life well in excess of one year, and may be used to prevent and/or treat disease or injury, such as oxidative stress related diseases and events.

12 Claims, 1 Drawing Sheet

(56) References Cited

OTHER PUBLICATIONS

AS Karakoti, SVNT Kuchibhatla, KS Babu, S Seal. "Direct Synthesis of Nanoceria in Aqueous Polyhydroxyl Solutions." Journal of Physical Chemistry C, vol. 111, 2007, pp. 17232-17240.*

G Czapski, BHJ Bielski, N Sutin. "The Kinetics of the Oxidation of Hydorgen Peroxide by Cerium(VI)." Journal of Physical Chemistry, vol. 67(1), 1963, pp. 201-203.*

Hohmann, Birgit, Authorized Officer, EPO, International Search Report of PCT/US2013/032318, Jun. 5, 2013.

Rzigalinski, Beverly A. Ph.D., "Nanoparticles and Cell Longevity," Technology in Cancer Research and Treatment, vol. 4, No. 6, pp. 651-659, Dec. 2005.

Masui, T. et al., "Synthesis of Cerium Oxide Nanoparticles by Hydrothermal Crystallization With Citric Acid," J. Mater. Sci. Lett. 21, pp. 489-491, 2002.

Hardas, Sarita et al., "Brain Distribution and Toxicological Evaluation of a Systemically Delivered Engineered Nanoscale Ceria," Toxicologial Sciences 116(2), pp. 562-576, 2010.

Karokoti, A.S. et al.; "Direct Synthesis of Nanoceria in Aqueous Polyhydroxyl Solutions," J. Physical Chem. C 111, pp. 17232-17240, 2007.

Karokoti, A.S. et al., "Nanoceria as Antioxidant: Systhesis and Biomedical Applications," Journal of the Minerals, Metals & Materials Society (JOM), 60(2), pp. 33-37, Mar. 2008.

Kim, Chi Kyung et al., "Ceria Nanoparticles That Can Protect Against Ischemic Stroke", Angew. Chem. Int., vol. 6, pp. 1-6, ED. 2012.

Estevez, A.Y. et al., "Neuroprotective Mechanisms of Cerium Oxide Nanoparticles in a Mouse Hippocampal Brain Slice Model of Ischemia," Free Radic. Biol. Med, 2011, doi:10.1016/j.freeradbiomed.2011.06.006.

"Metallic Nanocrystallites and Their Interaction With Microbial Systems"; Springer, XP002697256, Mar. 2, 2012.

Robert A. Yokel et al. "Biodistribution and Oxidative Stress Effects of a Systemically-Introduced Commercial Ceria Engineered Nanomaterial," Nanotoxicology, vol. 3, pp. 234-248, Sep. 2009.

* cited by examiner

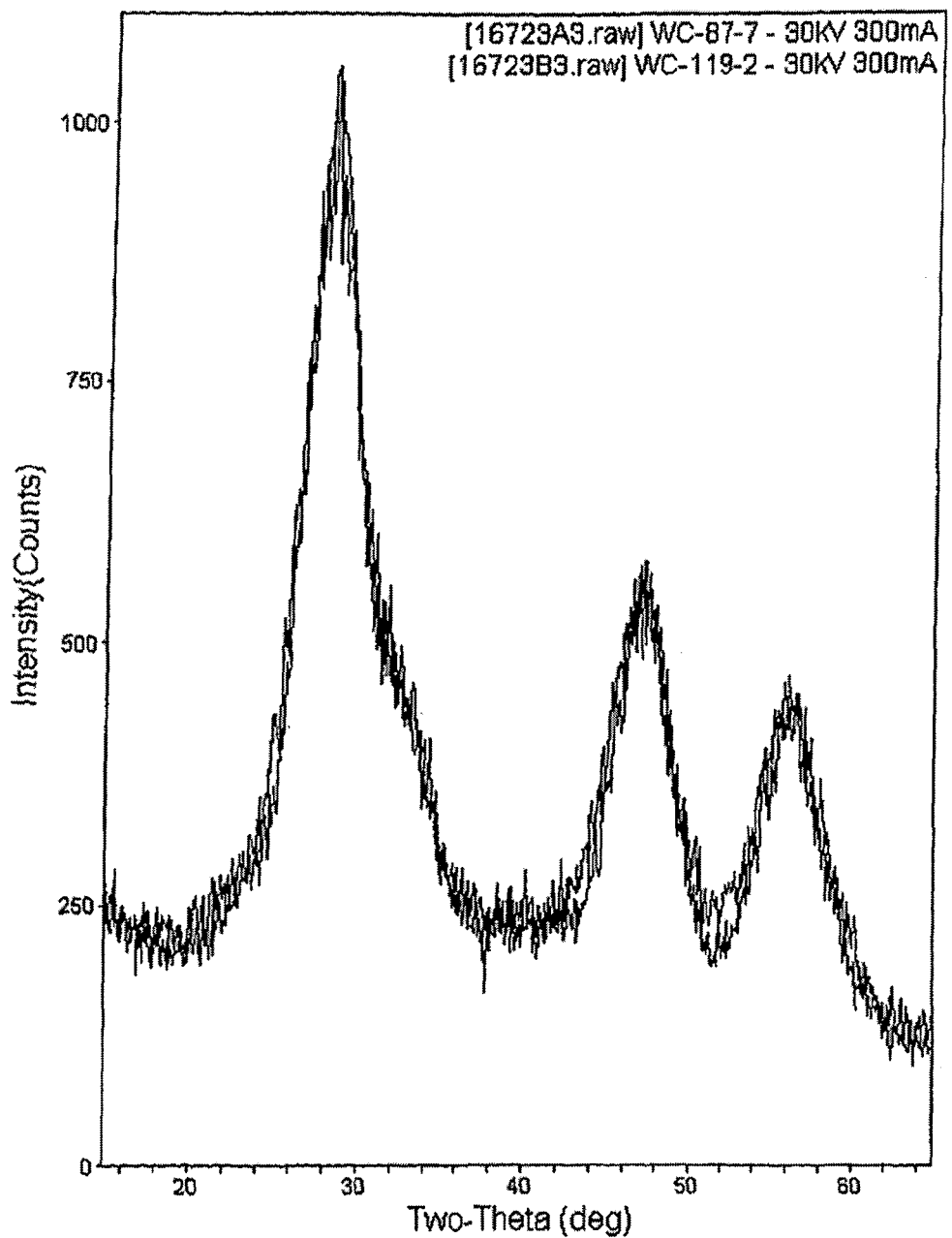

NANOCERIA WITH CITRIC ACID ADDITIVE

CROSS-REFERENCE TO RELATED APPLICATIONS

This patent application claims priority to Provisional Application Ser. No. 61/689,806, NANOCERIA FOR THE TREATMENT OF MULTIPLE SCLEROSIS, filed Jun. 13, 2012, the disclosure of which is incorporated herein by reference in its entirety.

FIELD OF THE INVENTION

The present invention relates in general to improvements in the field of nanoparticle preparations. In particular, the invention relates to cerium-containing nanoparticles prepared with citric acid, to methods of preparing such nanoparticles, and to the use of such nanoparticles to prevent and to treat inflammation and oxidative stress related events and diseases.

BACKGROUND OF THE INVENTION

Free radical oxidative stress plays a major role in the pathogenesis of many human diseases, and in particular, neurodegenerative diseases. Treatment with antioxidants, which may reduce particular free radical species, therefore, might theoretically prevent tissue damage and improve both survival and neurological outcome. Free radicals in physiological environments can often be classified as either a reactive oxygen species (ROS) or a reactive nitrogen species (RNS). Free radicals are highly reactive chemical species and readily react with proteins, lipids and nucleic acids at a subcellular level and thereby contribute to the progression of various diseases.

The origin of the use of nanoceria in nanomedicine can be traced to the seminal work of Bailey and Rzigalinski, wherein the application of ultrafine cerium oxide particles to brain cells in culture was observed to greatly enhanced cell survivability, as reported by Rzigalinski in Nanoparticles and Cell Longevity, *Technology in Cancer Research & Treatment* 4(6), 651-659 (2005). More particularly, rat brain cell cultures in vitro were shown to survive approximately 3-4 times longer when treated with 2-10 nanometer (nm) sized cerium oxide nanoparticles synthesized by a reverse micelle micro emulsion technique, as reported by Rzigalinski et al. in U.S. Pat. No. 7,534,453, filed Sep. 4, 2003. However, a host of problems with these particular nanoceria particles was subsequently reported by Rzigalinski et al. in WO 2007/002662. Nanoceria produced by this reverse micelle micro emulsion technique suffered from several problems: (1) particle size was not well-controlled within the reported 2-10 nanometer (nm) range, making variability between batches high; (2) tailing (carryover contamination) of surfactants, such as sodium bis(ethylhexyl)sulphosuccinate, also known as docusate sodium or (AOT), used in the process into the final product, caused toxic responses; (3) inability to control the amount of surfactant tailing posed problems with agglomeration when these nanoparticles were placed in biological media, resulting in reduced efficacy and deliverability; and (4) instability of the valence state of cerium (+3/+4) over time. Thus, the cerium oxide nanoparticles produced by the reverse micelle micro emulsion technique were highly variable from batch to batch, and showed higher than desired toxicity to mammalian cells.

As an alternative, Rzigalinski et al. in WO 2007/002662 reported the biological efficacy of nanoceria synthesized by various high temperature techniques, obtained from at least three commercial sources. These new sources of cerium oxide nanoparticles were reported to provide superior reproducibility of activity from batch to batch. It was further asserted that, regardless of source, cerium oxide particles having a small size, narrow size distribution, and low agglomeration rate are most advantageous.

Furthermore, Rzigalinski et al. also report that for delivery, the nanoparticles were advantageously in a non-agglomerated form. To accomplish this, they assert that stock solutions of about 10% by weight could be sonicated in ultra-high purity water or in normal saline prepared with ultra-high purity water. However, as others have noted, it has been observed that sonicated aqueous dispersions of nanoceria synthesized by high temperature techniques (e.g. obtained from commercial sources) are highly unstable, and settle rapidly (i.e. within minutes), causing substantial variability in administering aqueous dispersions of nanoceria derived from these sources.

While cerium oxide containing nanoparticles can be prepared by a variety of techniques known in the art, the particles typically require a stabilizer to prevent undesirable agglomeration.

In regard to biocompatible nanoceria stabilizers used previously. Masui et al., *J. Mater. Sci. Lett.* 21, 489-491 (2002) describe a two-step hydrothermal process that directly produces stable aqueous dispersions of ceria nanoparticles. Cerium chloride and citric acid are added with an excess of ammonia water. No oxidant is employed. High resolution TEM revealed that this form of nanoceria possessed crystalline polyhedral particle morphology with sharp edges and a narrow size distribution of 4-6 nm. However, this process is both time consuming and equipment intensive, requiring two separate 24 hours reaction steps, one of which requires a sealed reaction vessel, and the particles are reported to somewhat agglomerate with each other.

Hardas et al., *Toxicological Sciences* 116(2), 562-576 (2010) report the results of an extensive biodistribution and toxicology study performed in rats using the Masui et al. method of making citrate stabilized nanoceria. Hardas et al. report that aqueous dispersions of 5 nm average size nanoceria prepared by the direct two-step hydrothermal preparation of Masui et al. (described above) are stable for more than 2 months at a physiological pH of 7.35, and had a zeta potential of −53 mV. Therefore a sonication treatment prior to administration was not required.

Surprisingly, Hardas et al. report that compared to ~30 nm nanoceria (Sigma-Aldrich (#639648)), this smaller nanoceria was more toxic, was not seen in the brain, and produced little effect on oxidative stress in the hippocampus and cerebellum sections of the brain. The results were contrary to the hypothesis that smaller engineered nanomaterial would readily permeate the blood-brain barrier.

DiFrancesco et al. in commonly assigned PCT/US2007/077545, METHOD OF PREPARING CERIUM DIOXIDE NANOPARTICLES, filed Sep. 4, 2007, describes the oxidation of cerous ion by hydrogen peroxide at low pH (<4.5) in the presence of biocompatible stabilizers, such as citric acid, lactic acid, tartaric acid, ethylenediaminetetraacetic acid (EDTA), and combinations thereof. Specifically, the stabilizer lactic acid and the combination of lactic acid and EDTA are shown to directly produce stable dispersions of nanoceria (average particle size in the range of 3-8 nm), without an intermediate particle isolation step.

Karakoti et al. in *J. Phys. Chem. C* 111, 17232-17240 (2007) report a direct synthesis of nanoceria in mono/ polysaccharides by oxidation of cerous ion in both acidic conditions (by hydrogen peroxide) and basic conditions (by ammonium hydroxide). The specific biocompatible stabilizers reported include glucose and dextran. Individual particle sizes as small as 3-5 nm are reported, however, weak agglomerates of 10-30 nm result.

Karakoti et al. in JOM (Journal of the Minerals, Metals & Materials Society) 60(3), 33-37 (2008) comment on the challenge of synthesizing stable dispersions of nanoceria in biologically relevant media, so as to be compatible with organism physiology, as requiring an understanding of colloidal chemistry (zeta potential, particle size, dispersant, pH of solution, etc.) so as not to interfere with the reduction/oxidation (redox) ability of the nanoceria that enables the scavenging of free radicals (reactive oxygen species (ROS) and reactive nitrogen species). Karakoti et al. specifically describe the oxidation of cerium nitrate by hydrogen peroxide at low pH (<3.5) in the absence of any stabilizer, as well as, in the presence of dextran, ethylene glycol and polyethylene glycol (PEG) stabilizers. Particle sizes of 3-5 nm are reported, although particle agglomeration to 10-20 nm is also reported.

Thus, there remains a need for further improvements in methods for the direct preparation (i.e. without a particle isolation step) of biocompatible dispersions of nanoceria, for example, in a shorter period of time, that produce nanoparticles sufficiently small in size and uniform in size frequency distribution, and sufficiently resistant to agglomeration over long storage times to impart adequate shelf-life, for use, for example, as a pharmaceutical composition.

SUMMARY OF THE INVENTION

In accordance with a first aspect of the invention, a method of making a dispersion of nanoparticles is provided, comprising: forming a reaction mixture comprising cerous ion, citric acid, an oxidant, and water; adjusting the reaction mixture to a pH greater than 7.0 and less than about 10.0; optionally, heating or cooling the reaction mixture, and directly forming, without isolation, a dispersion of cerium-containing nanoparticles.

In various other embodiments of the method of first aspect of the invention, the oxidant used is hydrogen peroxide, the reaction mixture is subject to high shear mixing, the temperature of the reaction mixture is maintained at a temperature less than the boiling point of water, the cerium-containing nanoparticles produced are substantially crystalline and substantially non-agglomerated, the dispersion of cerium-containing nanoparticles has a zeta-potential ranging from about −15 mV to about −30 mV, and the dispersion has a shelf-life (i.e. stability) greater than about 6 months.

In a second aspect of the invention, a pharmaceutical composition is comprised of nanoparticles made by the method of the first aspect of the invention.

In a third aspect of the invention, methods of administering an effective amount of a pharmaceutical composition comprising cerium-containing nanoparticles made by the method of the first aspect of the invention, comprise administration, to a patient or subject, prior to or after the onset of a disease or injury. The disease or injury may include oxidative stress related diseases and events, such as ischemic stroke, traumatic brain injury, reperfusion injury, and central nervous system diseases, such as multiple sclerosis and amyotrophic lateral sclerosis.

BRIEF DESCRIPTION OF THE DRAWINGS

FIG. 1 contains powder X-ray diffraction (XRD) spectra of nanoparticles prepared with citric acid additive in Example 2, along with the spectrum of a known sample of nanoceria.

DETAILED DESCRIPTION OF THE INVENTION

It is to be understood that elements not specifically shown or described may take various forms well known to those skilled in the art. The invention is defined by the claims.

In this application, the term nanoparticle includes particles having a mean diameter of less than 100 nm. For the purposes of this disclosure, unless otherwise stated, the diameter of a nanoparticle refers to its hydrodynamic diameter, which is the diameter determined by dynamic light scattering technique and includes molecular adsorbates and the accompanying solvation shell of the particle. Alternatively, the geometric particle diameter can be estimated by analysis of transmission electron micrographs (TEM).

In this application, various cerium-containing materials are nominally described as "ceria", "cerium oxide" or "cerium dioxide." It will be understood by one skilled in the chemical arts, that the actual oxidic anions present in these materials may comprise oxide anions or hydroxide anions, or mixtures thereof, such as hydrated oxide phases (e.g. oxyhydroxide). In addition, it is known that compositions of matter may be comprised of solid solutions of multivalent cations, and are termed non-stoichiometric solids. Thus, for oxide phases comprised of metal cations of multiple oxidation states, it is understood that the total amount of oxidic anions present will be determined by the specific amounts of the various oxidation states of the metal cations present (e.g. $Ce^{3+}$ and $Ce^{4+}$), such that charge neutrality is maintained. For non-stoichiometric phases nominally described as metal dioxides, this is embodied in the chemical formula $MO_{2-\delta}$ wherein the value of $\delta$ (delta) may vary. For cerium oxides, $CeO_{2-\delta}$, the value of $\delta$ (delta) typically ranges from about 0.0 to about 0.5, the former denoting cerium (IV) oxide, $CeO_2$, the latter denoting cerium (III) oxide, $CeO_{1.5}$ (alternatively denoted $Ce_2O_3$). Alternatively, the value of $\delta$ (delta) denotes the amount of oxygen vacancies present relative to cerium (IV) oxide ($CeO_2$). For each oxygen di-anion vacancy present, two cerous ions ($Ce^{3+}$) are present, to preserve charge neutrality.

In one embodiment of the invention, a process is provided comprising: forming a reaction mixture comprising cerous ion, citric acid, an oxidant, and water; adjusting the reaction mixture to a pH greater than 5.0 and less than about 10.0; optionally heating or cooling the reaction mixture; and directly forming, without isolation, a stable dispersion of nanoparticles.

In a particular embodiment the reaction mixture is adjusted to a pH greater than 7.0. In various other embodiments, the reaction mixture is adjusted to a pH greater than 6.0 and less than about 10.0, greater than 6.0 and less than about 9.0, greater than 7.0 and less than about 10.0, greater than 7.0 and less than about 9.0, and greater than 8.0 and less than about 9.0.

In various embodiments, the molar ratio of citric acid to cerium ion in the reaction mixture is greater than about 6.0, greater than about 0.8, greater than about 1.0, greater than about 1.2, greater than about 1.4. In particular embodiments, the molar ratio of citric acid to cerium ion in the reaction mixture ranges from about 0.8 to about 3.2, from about 1.0 to about 2.8, from about 1.2 to about 2.4, and from about 1.4 to about 2.0.

In various embodiments, the oxidant includes compounds more oxidizing than molecular oxygen (or an ambient atmosphere of air). In particular embodiments, the oxidant has an aqueous half-cell reduction potential greater than −0.13 volts relative to the standard hydrogen electrode. In other embodiments the oxidant is an alkali metal or ammonium perchlorate, chlorate, hypochlorite or persulfate; ozone, a peroxide or a combination thereof. In a particular embodiment, a two-electron oxidant, such as hydrogen peroxide, is used. In particular embodiments, hydrogen peroxide is present in an amount greater than one-half the molar amount of cerous ion. In still other embodiments, the amount of oxidant present varies widely in relation to the amount of cerium ions or other metal ions present.

In particular embodiments, the temperature of the reaction mixture is greater than or less than ambient temperature. In particular embodiments, the reaction mixture is heated or cooled to temperatures greater than or less than ambient temperature. In various embodiments, the reaction mixture is heated or cooled to temperatures greater than about 30° C., greater than about 40° C., greater than about 50° C., or greater than about 60° C., greater than about 70° C., greater than about 80° C. or greater than about 90° C. In a particular embodiment, the reaction mixture is heated or cooled to a temperature less than the boiling temperature of water.

In a particular embodiment, the reaction mixture is maintained at ambient pressure.

In various embodiments, the nanoparticles formed are amorphous, partially crystalline or substantially crystalline, or highly crystalline. In a particular embodiment the nanoparticles formed are characterized by a cubic fluorite crystal structure. In a particular embodiment, the nanoparticles formed are characterized by a cerium oxide crystal structure.

As used herein, the terms semi-crystalline and substantially crystalline refer to nanoparticles that have at least some crystalline structure. As one of ordinary skill in the art recognizes, accurate characterization of particles becomes increasingly difficult as the particle size becomes smaller because smaller particles have less detectable long-range order.

In various embodiments, the reaction mixture is heated for a period of time less than 12 hours, less than 10 hours, less than 8 hours, less than 6 hours, less than 4 hours, less than 2 hours, less than 1.5 hours, and less than 1 hour.

In particular embodiments, the crystallinity of the nanoparticles formed is enhanced by heating of the reaction mixture.

In particular embodiments, the nanoparticles formed are dehydrated or dehydroxylated by heating of the reaction mixture.

In various embodiments, the nanoparticles formed have a hydrodynamic diameter less than 100 nm, less than 80 nm, less than 60 nm, less than 40 nm, less than 20 nm, less than 10 nm, less than 5.0 nm, less than about 3 nm or less than about 2.0 nm.

In a particular embodiment, the nanoparticles formed have a geometric diameter less than the hydrodynamic diameter.

In various embodiments, the nanoparticles formed have a coefficient of variation (COV) of the particle size, defined as the standard deviation of the particle size divided by the average particle size, less than about 15%, less than about 10%, less than about 5%, or less than about 3%.

In a particular embodiment, a nanoparticle comprising cerium is provided. In other embodiments, nanoparticles comprising a cerium oxide, a cerium hydroxide or a cerium oxyhydroxide are provided.

In a particular embodiment, a nanoparticle comprising citric acid and a cerium oxide, cerium hydroxide or cerium oxyhydroxide, is provided.

In other embodiments, a dispersion of cerium-containing nanoparticles having a zeta potential less than or equal to zero is provided. In particular embodiments, a nanoparticle comprising cerium oxide, citric acid, ethylenediaminetetraacetic acid and having a zeta potential less than or equal to zero is provided. In particular embodiments, a nanoparticle comprising cerium oxide, citric acid, and having a zeta potential less than −10 mV, less than −20 mV, less than −30 mV, or less than −40 mV while being greater than about −50 mV, is provided. In particular embodiments, a nanoparticle comprising cerium oxide, citric acid and having a zeta potential in the range of −15 mV to −30 mV, is provided.

In particular embodiments, a nanoparticle having a zeta potential greater than zero is provided. In particular embodiments, a nanoparticle comprising cerium, citric acid, ethylenediaminetetraacetic acid, and having a zeta potential greater than zero, greater than 10 mV, greater than 20 mV, greater than 30 mV, greater than 40 mV or greater than 50 mV, is provided.

In various embodiments, the zeta potential of the nanoparticles is altered by adjusting the pH, the citric acid content, for example to less than saturation coverage, or a combination thereof, of the nanoparticle dispersion.

In various embodiments, the dispersion of cerium-containing nanoparticles contains substantially non-agglomerated nanoparticles, greater than 90 percent non-agglomerated nanoparticles, greater than 95 percent non-agglomerated nanoparticles, greater than 98 percent non-agglomerated nanoparticles, and entirely non-agglomerated nanoparticles.

In a particular embodiment, the nanoparticle dispersion formed is washed to remove excess ions or by-product salts. In various embodiments, the nanoparticle dispersion is washed such that the ionic conductivity is reduced to less than about 15 millisiemens per centimeter (mS/cm), less than about 10 mS/cm, less than about 5 mS/cm or less than about 3 mS/cm. In particular embodiments, the nanoparticle dispersion formed is washed by dialysis, diafiltration or centrifugation.

In particular embodiments, the nanoparticle dispersions formed are concentrated to remove excess solvent or excess water. In particular embodiments, the nanoparticle dispersion is concentrated by dialysis, diafiltration or centrifugation.

In various embodiments, the concentration of nanoparticles in the dispersion is greater than about 0.05 molal, greater than about 0.5 molal or greater than about 2.0 molal (approximately 35% solids in a given dispersion).

In particular embodiments, the size distributions of the nanoparticles are substantially monomodal. In other embodiments, the nanoparticle size has a coefficient of variation (COV) less than about 30%, less than about 25%, less than about 20%, less than about 15%, less than about 10% or less than about 5%, where the COV is defined as the standard deviation divided by the mean.

In particular embodiments, various mixing devices known in the art are employed to stir, mix, shear or agitate the contents of the reaction mixture. In various embodiments, mixers comprising stir bars, marine blade propellers, pitch blade turbines or flat blade turbines are used.

In a particular embodiment, a high shear mixer, such as, but not limited to, a colloid mill or a Silverson® High Shear Mixer, is employed to subject the reaction mixture to high shear mixing. In a particular embodiment, a high shear mixer that forces the reaction mixture to pass through a screen comprising holes ranging in size from fractions of a millimeter to several millimeters is employed.

In particular embodiments, one or more of the reactants is introduced below the surface of the aqueous reaction mixture. In a particular embodiment, a reactant is introduced below the surface of the aqueous reaction mixture in close proximity to a mixing device.

In various embodiments, the shelf-life (i.e. stability) of the dispersion of cerium-containing nanoparticles is greater than 3 months, greater than 6 months, greater than 9 months, greater than 12 months, and greater than 15 months. Adequate shelf-life will vary with end-use application, but may include criteria such as, for example, stability with respect to change in nanoparticle agglomeration size and agglomeration amount, stability with respect to dispersion color, clarity and sediment formation.

In one embodiment of the invention, the aqueous nanoparticle dispersion is solvent shifted to a less polar solvent composition by methods disclosed in commonly assigned U.S. Patent Application Publication 2010/0152077, which is hereby incorporated by reference. In a specific embodiment, the nanoparticle dispersion is passed through a diafiltration column with an organic diluent comprising, for example, an alcohol or a glycol ether.

Without being bound by any theory, the proposed use of cerium oxides for the treatment of inflammation and oxidative stress related diseases (e.g. ROS mediated diseases) is based in part upon a belief that cerium oxides may function as catalytic scavengers of free radicals. The existence of and facile inter-conversion of cerium in a mixture of $Ce^{3+}$ and $Ce^{4+}$ valence states may enable cerium oxides to reduce and/or oxidize free radicals to less harmful species in a catalytic or auto-regenerative manner. Redox reactions may occur on the surface of cerium oxide nanoparticles that neutralize tissue-damaging free radicals. For example, it is believed to be desirable to oxidize superoxide anion ($O_2^-$) to molecular oxygen, to oxidize peroxynitrite anion ($ONOO^-$) to physiologically benign species, and to reduce hydroxyl radical (.OH) to hydroxide anion. This may in turn enable a greatly reduced dosing regimen in comparison to, for example, sacrificial antioxidants currently available to treat oxidative stress related diseases and events.

In particular embodiments, administered nanoceria particles of the invention are taken into cells through cell membranes and reside in the cellular cytoplasm or in various cellular organelles, such as the nucleus and mitochondria. In other embodiments, the nanoceria particles of the invention reside in intravascular or interstitial spaces, wherein they may reduce oxidative stress and inflammation by eliminating free radicals or reducing autoimmune responses. In a particular embodiment, the immune system invasion of the central nervous system resulting from breakdown of the blood-brain barrier (BBB) or blood-cerebrospinal fluid barrier (BCFB) or blood-ocular barrier (BOB) is modulated by nanoceria particles of the invention.

In another embodiment, the nanoceria particles of the invention are particles capable of crossing a mammalian blood brain barrier. In various embodiments, nanoceria particles of the invention cross a mammalian blood brain barrier and reside in brain parenchyma tissues as aggregates or agglomerates of a size less than about 100 nm, less than about 50 nm, less than about 20 nm, less than about 10 nm, less than about 5 nm. In a particular embodiment, nanoceria particles of the invention cross a mammalian blood brain barrier and reside in brain parenchyma tissues as independent, non-agglomerated nanoparticles of a size less than about 3.5 nm.

In particular embodiments, a pharmaceutical composition comprising nanoceria particles of the invention are specifically contemplated for prevention and/or treatment of oxidative stress related diseases and events, such as, but not limited to, Alzheimer's Disease, Parkinson's Disease, Huntington's Disease, amyotrophic lateral sclerosis (ALS), ataxia, Friedreich's ataxia, autism, obsessive-compulsive disorder, attention deficit hyperactivity disorder, migraine, stroke, traumatic brain injury, cancer, inflammation, autoimmune disorders, lupus, MS, inflammatory bowel disease, Crohn's Disease, ulcerative colitis, stenosis, restenosis, atherosclerosis, metabolic syndrome, endothelial dysfunction, vasospasms, diabetes, aging, chronic fatigue, coronary heart disease, cardiac fibrosis, myocardial infarction, hypertension, angina, Prizmetal's angina, ischemia, angioplasty, hypoxia, Keshan disease, glucose-6-phosphate dehydrogenase deficiency, favism, ischemic reperfusion injury, rheumatoid and osteo-arthritis, asthma, chronic obstructive pulmonary disease (e.g. emphysema and bronchitis), allergies, acute respiratory distress syndrome, chronic kidney disease, renal graft, nephritis, ionizing radiation damage, sunburn, dermatitis, melanoma, psoriasis, macular degeneration, retinal degeneration, cataractogenesis, among others.

In particular embodiments, a pharmaceutical composition comprising nanoceria particles of the invention are specifically contemplated for prevention and/or treatment of oxidative stress related cellular pathologies, such as, but not limited to, mitochondrial dysfunction, lysosome and proteasome dysfunction, oxidation of nucleic acids (e.g. RNA and DNA), tyrosine nitration, loss of phosphorylation mediated signaling cascades, initiation of apoptosis, lipid peroxidation and destruction of the membrane lipid environment.

In at least one embodiment, a pharmaceutical composition comprising cerium-containing nanoparticles made in accordance with the present invention are administered in an effective amount to prophylactically treat an oxidative stress related disease. As used herein, the phrase "effective amount" means an amount of a pharmaceutical composition comprising sufficient active principle (e.g. cerium-containing nanoparticles) to bring about the desired effect. The pharmaceutically acceptable amount, as recognized in the art, can be determined through routine experimentation.

In at least one embodiment, a pharmaceutical composition comprising cerium-containing nanoparticles made in accordance with the present invention are administered in an effective amount to treat symptoms of an oxidative stress related disease.

In various embodiments, a pharmaceutical composition comprising nanoceria particles of the invention is administered to a human or a non-human subject, such as another mammal, including, but not limited to, a canine, a feline, a bovine, an equine, an ovine, a porcine or a rodent. Alternatively, the subject of administration can be an animal such as a bird, insect, reptile, amphibian, or any companion or agricultural animal.

In various embodiments, nanoceria particles of the invention are administered in vivo to a subject by topical, enteral or parenteral methods, including injections, infusions or implantations. More particularly, it is specifically contemplated to administer nanoceria particles of the invention to a subject by any of the following routes: auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intrabiliary, intrabronchial, intrabursal, intracardiac, intracartilaginous, intracaudal, intracavernous, intracavitary, intracerebral, intracisternal, intracorneal, intracornal-dental, intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmammary, transmucosal, transplacenta, transtracheal, transtympanic, ureteral, urethral, vaginal, and any other or unassigned route.

In other embodiments, nanoceria particles of the invention are retained in or on the surface of a medical device or prosthesis, such as a cannula, catheter or stent, thereby reducing inflammation locally or systemically, over either a short or long time period.

In various embodiments, the nanoceria particles of the invention are delivered in any suitable form known in the art, including, but not limited to, a suspension, gel, capsule, tablet, enteric coated tablet, loaded liposome, powder, suppository, infusible, lozenge, cream, lotion, salve, or inhalant.

In various embodiments, the nanoceria particles of the invention are combined with other pharmaceutically acceptable substances, such as, but not limited to, water, salts, buffers, phosphate buffered saline (PBS), sugars, human or bovine serum albumen, lipids, drugs, colorants, flavorants, binders, gums, surfactants, fillers or any excipients known in the art.

In a particular embodiment, the vehicle comprising the nanoceria particles of the invention is sterilized prior to administration.

In other embodiments, a cell or cell culture is contacted with a nanoceria particle or particles of the invention. Contact may be practiced by exposing a cell or cell culture by in vitro or ex vivo methods, wherein the latter method comprises re-introducing the treated cell or cells into a subject, such as the subject from which the cell or cells were originally obtained. In various embodiments the cell is prokaryotic or eukaryotic in nature. In particular embodiments, the treated cells are used in the production of proteins used in the pharmaceutical industry, generally known as biologics, such as, but not limited to, antigens, antibodies and vaccines. In another embodiment, the treated cells are used in a fermentation process.

The invention is further illustrated by the following examples, which are not intended to limit the invention in any manner.

EXPERIMENTAL SECTION

Nanoparticle Light Scattering and Size Assessments

A simple qualitative characterization of the particle dispersions was performed by assessing the degree of Tyndell scattering exhibited by the dispersions when illuminated by a red laser pen light, relative to the amount of scattering from a sample of the neat solvent. A quantitative assessment of the particle size of the nanoparticle dispersions was performed by dynamic light scattering (DLS) using a Brookhaven 90Plus Particle Size Analyzer (Brookhaven Instruments Corp., Holtzville, N.Y., U.S.A.) equipped with a quartz cuvette. Reported DLS sizes are the lognormal number weighted parameter.

Nanoparticle Charge Assessment

A quantitative assessment of the nanoparticle charge was made by measuring the zeta potential of the dispersion using a Zetasizer Nano ZS from Malvern Instruments.

Example 1

Nanoceria Preparation with Citric Acid Additive at pH 6.5

To a 3 liter round bottom stainless steel reactor vessel was added 1017 grams of distilled water. A high-shear radial-flow mixer (Lightnin® R100 Rushton style turbine) was lowered into the reactor vessel such that the mixer head was positioned slightly above the bottom of the reactor vessel. The mixer speed was set to 700 rpm, and the reactor was brought to a temperature of 85° C. 150 ml of 1.25M Citric Acid monohydrate solution was added and allow to blend. A double jet addition was conducted over a period of five minutes by pumping a 250 ml solution containing 0.29 moles $Ce(NO_3)_3.6H_2O$ into the reactor concurrently with a solution containing 69.5 grams of (28-30%) ammonium hydroxide. A distilled water chase into the reactor cleared the reactant lines of residual materials. Then a 200 ml solution containing 20.4 grams of 50% non-stabilized hydrogen peroxide was added to the reactor and its contents over a period of 10 minutes. The reaction mixture was at a pH of about 6.5. The reaction mixture was heated for an additional 60 minutes at 85° C., during which time the pH dropped only slightly, to about 6.2. The reaction was cooled to 20° C. and diafiltered to a conductivity of 5 mS/cm to remove excess water and unreacted materials.

The final product dispersion was a clear yellow/orange liquid that displayed a high degree of Tyndall scattering when illuminated with a low intensity LASER beam, indicating it contained well-dispersed colloidal particles. Particle size analysis by dynamic light scattering indicated a hydrodynamic diameter of 12.4 nm.

A dispersion stability test was undertaken to assess the shelf-life. After 11 days a substantial layer of sediment had formed. A sample of the supernatant was tested by dynamic light scattering and the hydrodynamic diameter had increased to 41.5 nm.

Example 2

Nanoceria Preparation with Citric Acid Additive at pH 8.5

Into a 800 ml glass beaker containing a magnetic stir bar was introduced 500 ml of high purity (HP) water. The water was then heated to about 70° C., and therein 7.74 grams of citric acid was dissolved. Ammonium hydroxide (28-30%) was added to adjust the pH of the solution to about 8.5. The temperature of the reaction vessel was raised to about 80° C., and the magnetic stir bar was replaced with a Silverson®

L4RT high shear mixer operated at 5000 rpm. A 10.0 gm quantity of $Ce(NO_3)_3.6(H_2O)$ was dissolved in 30 ml of HP water, and this solution was added slowly to the stirred reaction mixture over several minutes. The reaction pH was maintained at about 8.5 by addition of small amounts of conc. $NH_4OH$ solution. Then a 50 ml solution containing 4.8 ml of 50% $H_2O_2$ was added slowly over several minutes to the cerous ion and citric acid reaction mixture. The reaction product was covered and then heated for an additional hour, resulting in a clear yellow/orange suspension. After cooling with stirring, the directly formed nanoparticle dispersion was washed by diafiltration to an ionic conductive of less than about 10 mS/cm, to remove excess salts. The pH of the product dispersion was about 7.2.

The final product dispersion was a clear yellow/orange liquid that displayed a high degree of Tyndall scattering when illuminated with a low intensity LASER beam, indicating it contained well-dispersed colloidal particles. Particle size analysis by dynamic light scattering indicated a hydrodynamic diameter of 7.8 nm.

A sample of the product dispersion was submitted for phase identification and crystallite size analysis by powder X-ray diffraction (XRD). Sample portions were placed in a Teflon boat, dried under a heat lamp for four hours, and then dried in an oven for four hours at 80° C. under vacuum. The resulting solids were lightly ground to form powders. These powders were then front-packed onto glass holders and analyzed by XRD in a $N_2$ dry cell attachment.

A comparison of the XRD spectra with that of a known sample of nanoparticulate $CeO_2$ is shown in FIG. 1, which reveals a virtually identical match over the 15 to 65 degrees Two-Theta range examined. This confirmed the crystalline structural phase identification as cerium dioxide. An average crystallite size of 2.2 nm in the $CeO_2$ (220) direction was determined for the sample using the Scherrer technique.

Measurement of the zeta-potential indicated a nanoparticle charge of −20.8 mV.

A dispersion stability test was undertaken to assess the shelf-life. After 18 months the dispersion had remained clear and free of any sediment, and was unchanged in color.

Example 3

Nanoceria Preparation with Citric Acid at pH 8.5 with Low Shear Mixing

The procedures of Example 2 were repeated, except that the high shear mixer was replaced with a low shear magnet stir bar mixing system. Substantially similar results were obtained for particle size and zeta-potential, in that a hydrodynamic diameter of 7.0 nm was obtained by DLS along with a zeta-potential of −19.4 mV. Electron diffraction spectra revealed significantly broader diffraction bands for the nanoceria particles formed under the low shear mixing condition, suggesting that the nanoparticles were less crystalline relative to those produced under the high shear conditions of Example 2.

Impact of Nanoceria on Ischemic Stroke

Mouse Hippocampal Brain Slice Model of Ischemic Stroke

The ability of nanoceria to reduce oxidative stress was evaluated in a modification of the in vitro mouse hippocampal brain slice model of ischemia described by Estevez, A Y; et al., Neuroprotective mechanisms of cerium oxide nanoparticles in a mouse hippocampal brain slice model of ischemia, *Free Radic. Biol. Med.* (2011)51(6):1155-63 (doi: 10.1016/j.radbiomed.2011.06.006).

Adult (2-5 months of age) CD1 mice were sacrificed via rapid decapitation and their brains quickly removed and placed in a chilled choline-based slicing solution containing 24 mM choline bicarbonate, 135 mM choline chloride, 1 mM kynurenic acid, 0.5 mM $CaCl_2$, 1.4 mM $Na_2PO_4$, 10 mM glucose, 1 mM KCl, and 20 mM $MgCl_2$ (315 mOsm). Transverse hippocampal slices, 400 µm thick, were cut along a rostral-to-caudal axis (−1.2 to −2.8 mm Bregma) using a Leica VT1200 Vibratome (Leica Microsystems, Wetzlar, Germany) and allowed to recover for 1 hr in a control artificial cerebral spinal fluid (aCSF) containing 124 mM NaCl, 3 mM KCl, 2.4 mM $CaCl_2$, 1.3 mM $MgSO_4$, 1.24 mM $K_3PO_4$, 26 mM $NaHCO_3$, 10 mM glucose and bubbled with 5% $CO_2$, 95% $O_2$ gas (pH 7.4, 300 mOsm). Hippocampal slices were placed in a culture dish and stored in a NuAire humidified incubator (NuAire, Plymouth, Minn., USA) at 37° C. with 5% $CO_2$ for up to 48 hr.

Oxidative stress from ischemia was induced by placing the brain slices in hypoglycemic, acidic and hypoxic aCSF (glucose and pH were lowered to 2 mM and 6.8, respectively, and the solution was bubbled with 84% $N_2$, 15% $CO_2$, and 1% $O_2$) at 37° C. for 30 min. Sucrose was added to maintain the osmolarity of the solution at about 295 mOsm.

Aqueous dispersions of cerium oxide nanoparticles prepared as described supra were administered in matched dosage in a delivery volume of 1 µg per 1 ml aCSF or medium (equivalent to 5.8 µM) at the onset of the ischemic event, and remained in the medium throughout the remainder of the experiment. Control slices received an equal volume of vehicle control. Various delivery vehicles were used with similar success for the cerium oxide nanoparticles prepared as described herein, including distilled water alone, saline solution, Na-citrate solution, PBS, and combinations thereof.

After exposure to 30 minutes of oxidative stress (ischemic conditions), the living brain slices (test and control) were incubated for 24 hr in organotypic culture by placing them in a 35 mm culture dish containing culture medium and Millipore inserts (Millipore, Billerica, Mass., USA). Culture medium contained 50% minimum essential medium (Hyclone Scientific, Logan Utah, USA), 25% horse serum, 25% Hank's balanced salt solution (supplemented with 28 mM glucose, 20 mM HEPES and 4 mM $NaHCO_3$), 50 U/ml penicillin, and 50 µl/ml streptomycin, pH 7.2.

The extent of cell death was measured 24 hours after the oxidative injury using fluorescence imaging techniques. Each set of brain slices studied in the test condition (i.e. administered with cerium oxide nanoparticles) was matched with a similar set of control brain slices treated identically in every way except for administration of vehicle alone. Thus on each study day, two sets of anatomically matched brain slices taken from age-matched and sex-matched littermates were subjected to either the test condition (administered with cerium oxide nanoparticles) or control (vehicle alone). During fluorescence imaging measurements, the light intensity, duration of image capture, and timing of image collection were identical for the test condition and vehicle control brain slices. Results were expressed as the ratio of the fluorescence in the test condition to the fluorescence in the matched control slice imaged at the same time point in the experimental sequence.

At 24 hours post oxidative injury, paired (control and test) brain slices were incubated for 20 min in culture medium containing 0.81 µM vital exclusion dye SYTOX® Green (Invitrogen, Carlbad, Calif., USA) and, subsequently, washed for 15-20 min in culture medium to remove unincorporated dye. SYTOX® Green is a fluorescent dye that binds to DNA and RNA. However, it is excluded from the cell nucleus by the cell membrane in intact, viable cells. Therefore, it acts as a vital dye and stains only those dead and dying cells in which the cell membrane has become permeable so that the dye has access to the cell interior. After staining and washing, brain slices were transferred to the stage of a Nikon TE 2000-U (Nikon Instruments, Melville, N.Y., USA) microscope equipped with epifluorescence attachments and a 150-W xenon light source (Optiquip, Highland Mills, N.Y., USA). Control aCSF solution was loaded into 60-ml syringes, equilibrated with 95% $O_2$/5% $CO_2$, and heated to 37° C. using a servo-controlled syringe heater block, stage heater, and in-line perfusion heater (Warner Instruments, Hamden, Conn., USA). The brain sections were continuously perfused with warmed, 95% $O_2$/5% $CO_2$ equilibrated aCSF at a rate of 1 ml per minute. After 5 min, images of the hippocampal formation of each control and test brain slice were collected using a 4× Plan Flour objective (Nikon Instruments) under identical conditions (i.e. light intensity, exposure time, camera acquisition parameters). SYTOX® Green fluorescence was measured by briefly (620 ms) exciting the tissue at 480±40 nm, filtering the emitted fluorescence (535±50 nm) from the probe using a 505 nm, long-pass, dichroic mirror (Chroma technology, Bennington, Vt., USA), intensifying, and measuring with a cooled CCD gain EM camera (Hamamatsu CCD EM C9100; Bridgewater, N.J., USA). The digital images were acquired and processed with Compix SimplePCI 6.5 software (C Imaging Systems, Cranberry Township, Pa., USA).

The light intensity resulting from the SYTOX® Green loading reflected the number of dead or dying cells within the calculated area. The light-intensity measurements were performed automatically using the Compix SimplePCI 6.5 software, thereby eliminating experimenter bias in selecting the regions of interest.

Reduction in cell death is reported as the ratio of the light intensity of SYTOX® Green fluorescence from the cornu ammonis fields (oriens layer, stratum radiatum and lacunosum moleculare) for the test condition (i.e. nanoceria treated) to the control (untreated) for anatomically matched hippocampal sections taken from age-matched and sex-matched littermate brains sliced and exposed to ischemic oxidative stress on the same day, and fluorescence imaged 24 hr after the ischemic insult.

A sample of the dispersion of cerium dioxide nanoparticles prepared in Example 2 was evaluated in the Mouse Hippocampal Brain Slice Model of Ischemic Stroke using a treatment concentration of 5.8 µM. Treatment with the nanoparticle dispersion of Example 2 resulted in a 15.5% reduction in cell death relative to vehicle control. This result clearly demonstrated the ability of a cerium-containing nanoparticle dispersion prepared according to a process of the invention to reduce the effects of an oxidative stress event in the form of an ischemic stroke.

In summary, a comparison of the results between Examples 1 and Example 2 described above indicated that the embodiment prepared at a reaction pH of 8.5 resulted in improved (reduced) particle size, dramatically improved dispersion stability (increased shelf-life) and utility in reducing the effects of oxidative stress in a model of ischemic stroke. Comparison of Examples 2-3 suggested that use of the high shear mixing conditions produced nanoceria particles with a higher degree of crystallinity.

While the invention has been described by reference to various specific embodiments, it should be understood that numerous changes may be made within the spirit and scope of the inventive concepts described. Accordingly, it is intended that the invention not be limited to the described embodiments, but will have the full scope defined by the claims.

What is claimed:

1. A method of making a dispersion of nanoparticles, comprising forming a reaction mixture comprising cerous ion, citric acid, hydrogen peroxide and water at a pH greater than 7.0 and less than 10.0, thereby directly forming, without isolation, a dispersion of cerium-containing nanoparticles.

2. The method of claim 1, wherein the molar ratio of citric acid to cerous ion is greater than about 0.8.

3. The method of claim 1, further comprising subjecting said reaction mixture to high shear mixing.

4. The method of claim 1, wherein said cerium-containing nanoparticles are substantially crystalline.

5. The method of claim 1, further comprising heating or cooling the reaction mixture to maintain a reaction temperature less than the boiling temperature of water.

6. The method of claim 1, wherein said cerium-containing nanoparticles are substantially non-agglomerated.

7. The method of claim 1 wherein greater than about 90 percent of said cerium-containing nanoparticles are non-agglomerated.

8. The method of claim 1, wherein said dispersion of cerium-containing nanoparticles has a zeta-potential ranging from about −15 mV to about −30 mV.

9. The method of claim 1, wherein said dispersion of cerium-containing nanoparticles has a shelf-life greater than six months.

10. The method of claim 1, wherein the nanoparticles have a size less than about 3.5 nm.

11. The method of claim 1, wherein the pH of the reaction mixture is 8.5.

12. The method of claim 1, further comprising adding ammonium hydroxide to the reaction mixture.

* * * * *